United States Patent [19]

Howard

[11] Patent Number: 4,822,564
[45] Date of Patent: Apr. 18, 1989

[54] CHEMILUMINESCENT GAS ANALYZER FOR MEASURING THE OXIDES OF NITROGEN

[75] Inventor: Charles P. Howard, Ann Arbor, Mich.

[73] Assignee: Sensors, Inc., Saline, Mich.

[21] Appl. No.: 12,077

[22] Filed: Feb. 6, 1987

Related U.S. Application Data

[63] Continuation-in-part of Ser. No. 751,215, Jul. 2, 1985, Pat. No. 4,657,744.

[51] Int. Cl.⁴ .............................................. G01N 21/76
[52] U.S. Cl. ................................ 422/52; 250/361 C; 436/116; 436/172
[58] Field of Search .......... 422/52; 436/172, 106–118; 250/361 C

[56] References Cited

U.S. PATENT DOCUMENTS

| | | | |
|---|---|---|---|
| 3,710,107 | 1/1973 | Warren et al. | 250/71.5 |
| 3,746,513 | 7/1973 | Warnick et al. | 23/232 |
| 3,795,489 | 3/1974 | Warnick et al. | 422/52 |
| 3,848,128 | 11/1974 | McMillan, Jr. | 422/52 |
| 3,849,653 | 11/1974 | Sakaide et al. | 250/361 |
| 3,856,473 | 12/1974 | Dillon | 23/254 |
| 3,871,767 | 3/1975 | Holm-Hansen et al. | 356/215 |
| 3,917,454 | 11/1975 | Clark | 23/232 R |
| 3,938,390 | 2/1976 | Grey | 73/421 |
| 3,963,928 | 6/1976 | Zolner | 250/361 |
| 3,967,933 | 7/1976 | Etess et al. | 23/232 E |
| 4,004,882 | 1/1977 | Byrne et al. | 23/254 R |
| 4,190,368 | 2/1980 | Etess | 356/417 |
| 4,236,895 | 12/1980 | Stahl | 23/232 R |
| 4,333,735 | 6/1982 | Hardy et al. | 422/52 |
| 4,386,534 | 6/1983 | Englund | 73/863.01 |
| 4,657,744 | 4/1987 | Howard | 422/52 |

FOREIGN PATENT DOCUMENTS 2508149 8/1975 Fed. Rep. of Germany.
3029092 2/1982 Fed. Rep. of Germany.

OTHER PUBLICATIONS

Delaney et al., "Modification of a Commercial NO$_X$ Detector for High Sensitivity", published Dec. 1982.
Stedman, D. H. et al., "Analysis of Ozone & Nitric Oxide by a Chemiluminescent Method in Laboratory & Atmospheric Studies of Photochemical Smog"-published 4/4/72.
Steffenson, D. M. et al., "Optimization of the Operating Parameters of Chemiluminescent Nitric Oxide Detectors"-published 10/74.
Stedman, Donald H. et al., "Instrumental Analysis in Environmental Chemistry-Gas Phase Detection Systems", published 5/1984.

*Primary Examiner*—Michael S. Marcus
*Attorney, Agent, or Firm*—Price, Heneveld, Cooper, DeWitt & Litton

[57] ABSTRACT

A gas analyzer for determining the concentration of the oxides of nitrogen in a sample gas is provided. The analyzer is particularly adapted for analyzing the exhaust from an internal combustion engine. In one embodiment, the analyzer comprises a sample chamber and a reference chamber. An arrangement is provided for delivering sample gas containing the lower oxide of nitrogen (NO) to the sample chamber and a quantity of ozone ($O_3$) for reacting with this oxide of nitrogen and producing a chemiluminescence. After the chemiluminescence is completed, the sample gas is discharged to the reference chamber. A sample photodiode is disposed adjacent to the sample chamber for receiving light emitted from the sample chamber and producing a sample signal representative of the total photoemissivity of the sample gas. A reference photodiode is disposed adjacent to the reference chamber for receiving light emitted from the reference chamber and providing a reference signal representative of the dark current of the photodiodes and the background photoemissivity of the sample gas. A circuit is provided for conditioning and substracting the sample signal and the reference signal to produce an output representative of the concentration of the oxide of nitrogen in the sample gas. Dilution air is mixed with the sample gas either in the instrument with a viscous metering technique or in a sample probe, mounted in the exhaust of the engine, with a sonic metering technique. In other embodiments, a single sample photodiode is used to measure the chemiluminescent reaction and determine the oxide of nitrogen content of the sample gas.

45 Claims, 9 Drawing Sheets

CHEMILUMINESCENT GAS ANALYZER FOR MEASURING THE OXIDES OF NITROGEN

This application is a continuation-in-part application of copending patent application Ser. No. 751,215, filed July 2, 1985 entitled CHEMILUMINESCENT GAS ANALYZER FOR MEASURING THE OXIDES OF NITROGEN, now U.S. Pat. No. 4,657,744.

BACKGROUND OF THE INVENTION

The invention relates generally to a gas analyzer for determining the concentration of the oxides of nitrogen in a sample gas and more particularly is directed to a chemiluminescence NO, $NO_2$, $NO_x$ analyzer for determining the concentration of the oxides of nitrogen in the exhaust gas of a combustion engine or power plant.

While there are five oxides of nitrogen, there are only two that are of primary concern with regard to the emissions from a combustion engine; namely NO (nitric oxide) and $NO_2$ (nitrogen dioxide). The total of the emissions of the oxides of nitrogen is generally referred to as $NO_x$. Existing and forthcoming legislative measures both in the U.S. and Europe have created a need for an inexpensive and accurate analyzer for monitoring the oxides of nitrogen emissions of automotive engines. Similarly, there is much interest in monitoring the emissions from stationary power plants, or the like, and monitoring ambient concentrations of the oxides of nitrogen. Most of the $NO_x$ emitted by gasoline engines is NO which slowly oxides to $NO_2$. However, in some combustion engines, such as in a diesel engine where compression ratios are higher and air fuel ratios are leaner, a substantial amount of $NO_2$ is formed directly during the combustion process.

There are a number of possible techniques for measuring NO concentrations. These include nondispersive, infrared or ultraviolet gas analysis. However, infrared gas analysis of NO is difficult because of the absorptivity of NO lies in a range where there is interference with water vapor. While NO has a very strong ultraviolet absorption line where water vapor would not act as a contaminate, nondispersive ultraviolet analysis has not been successful because a very selective source of ultraviolet energy is required and the sources which have been developed to date have a very short life span. The most popular technique for measuring NO in the prior art involves the principle of chemiluminescence. Chemiluminescence involves the oxidation of NO to $NO_2$ instantaneously with $0_3$ (ozone). When this occurs, the $NO_2$ which is formed is in an excited state and it immediately returns to its ground state giving off a photon. The photon emission of the $NO_2$ returning to its ground state is proportional to the amount of NO in the sample gas as long as stoichiometric or greater quantities of ozone are present. The reaction takes place in approximately 10 milliseconds and for practical purposes is considered instantaneous. Thus, gas analyzers are found in the prior art which measure this chemiluminescent reaction with a photomultiplier for the purpose of producing a signal which is representative of the NO concentration in a sample gas.

In fact, the use of chemiluminescent nitric oxide detectors has become widespread in the prior art. The typical applications for such detectors are in air pollution monitoring instruments and gas analyzers for determining atmospheric concentrations of the oxides of nitrogen or the concentrations of the oxides of nitrogen in auto gas emissions, power plant emissions, etc. The success of prior art chemiluminescent detectors has almost lead to the adoption of such instruments as de facto legislative standards. However, these prior art chemiluminescent oxides of nitrogen gas analyzers have inherent problems which stem from the use of a photomultiplier for measuring the chemiluminescent reaction. Photomultipliers are vacuum tube devices which are large, fragile and expensive. It is generally difficult to supply such a tube with adequate air flow for cooling and lowering the dark current while at the same time meeting shielding requirements with regard to ambient light and radio frequency energy which substantially interfere with the operation of the device. In some prior art analyzers of this type, a thermoelectric cooled photomultiplier tube is used. While this results in an instrument having good performance, the cost of the instrument is high. Still further, although the gain of a photomultiplier tube is high, because the tube comprises a plurality of plates arrayed within a glass envelope, it is difficult to place the detector plates within close proximity to the chemiluminescent reaction. Since the photons issuing from the chemiluminescent reaction are very dispersive and difficult to focus, this can have a deleterious effect on detector sensitivity. Other problems with prior art chemiluminescent detectors in general relate to the fact that the sample gas under investigation normally contains large amounts of $CO_2$ which has a quenching effect on the chemiluminescent reaction. The ozone requirements of these instruments is relatively high, and ozone is itself a noxious gas. The range of these instruments can be somewhat limited, and in cases where a hot gas sample is drawn from exhaust of a combustion engine, water condensate can interfere with the operation of the instrument.

SUMMARY OF THE INVENTION

According to the present invention, these and other problems in the prior art are solved by the provision of a chemiluminescent oxides of nitrogen gas analyzer which in one embodiment features a pair of small, inexpensive and durable photodiodes for measuring the chemiluminescent reaction. In other embodiments a single photodiode is used. According to another important aspect of the present invention, $CO_2$ quenching is reduced, the instrument is provided with an extended range, ozone requirements are reduced and water condensate is substantially eliminated by mixing dilution air with the sample gas.

In one embodiment, the gas analyzer comprises a sample chamber, an arrangement for delivering the sample gas of interest to the sample chamber and an arrangement for delivering a sufficient quantity of ozone to the sample chamber for reacting with NO and producing a chemiluminescence. A sample photodiode is disposed adjacent to the sample chamber for receiving light emitted from the sample chamber and producing a sample signal representative of the total photoemissivity of the sample gas disposed in the sample chamber. A reference chamber is provided, the reference chamber being disposed immediately adjacent to the sample chamber. A cross port is provided between the sample chamber and the reference chamber for discharging the sample gas to the reference chamber after the chemiluminescent reaction is completed. A reference photodiode is disposed adjacent the reference chamber for receiving light emitted from the reference chamber and providing a reference signal representative of both the dark current of the sample photodiodes and the background photoemissivity of the sample gas in question. The sample and reference diodes are provided with an isothermal relationship. Processing circuitry is provided for the photodiodes which includes a sample voltage follower and a reference voltage follower having high input impedances and low current leakage.

Thereafter, a differential amplifier determines the difference between the output of the sample voltage follower and the reference voltage follower to provide an accurate measure of NO concentration compensated for detector noise or dark current and compensated for the background photoemissivity of the sample gas. In most cases, the $NO_2$ concentration can be inferred from the NO concentration and total $NO_x$ can be estimated. However, in those cases where it is desirable to measure total $NO_x$ concentration, a catalyst is provided for reducing $NO_2$ to NO prior to the chemiluminescent reaction NO concentration can be subtracted from $NO_x$ concentration to provide an accurate measure of $NO_2$. High-speed low capacitance planar diffusion type photodiodes are used which are small, inexpensive, durable, easily cooled, easily shielded and which feature a planar light sensitive surface which can be disposed directly adjacent to the chemiluminescent reaction to increase sensitivity.

According to another important aspect of the present invention, an arrangement is provided for introducing dilution air into the sample gas prior to delivery of the sarple gas to the sample chamber. In one embodiment of the invention, the dilution air is introduced in the instrument with a viscous metering technique to provide a predetermined dilution ratio of air to sample gas. In another embodiment of the invention, the analyzer is provided with a sample probe, which is adapted for insertion in the exhaust gas of a combustion engine, and dilution air is injected in the sample probe, at the exhaust gas pressure, with a sonic metering technique. In both embodiments of the invention, dilution of the sample gas substantially eliminates $co_2$ quenching, extends the range of the instrument, reduces the ozone requirements of the instrument and reduces problems with water condensate in the sample gas.

In still other embodiments of the invention, the sample and reference photodiodes may be heated and maintained at a constant temperature to stabilize the output span of the instrument. In embodiments where the sample photodiode is held at a constant temperature, the reference photodiode may be eliminated and only a single sample photodiode may be used, further reducing the cost and complexity of the instrument. The accuracy of the instrument is also improved in some embodiments by providing an arrangement for supplying dry air to an ozone generator. The use of dry air in the ozone generator reduces the need for dilution air, enabling a reduction of dilution ratio to a range of 5:1 through 2:1 of air to sample, thereby improving the resolution of the instrument.

DESCRIPTION OF THE PREFERRED EMBODIMENTS

Figure 1:
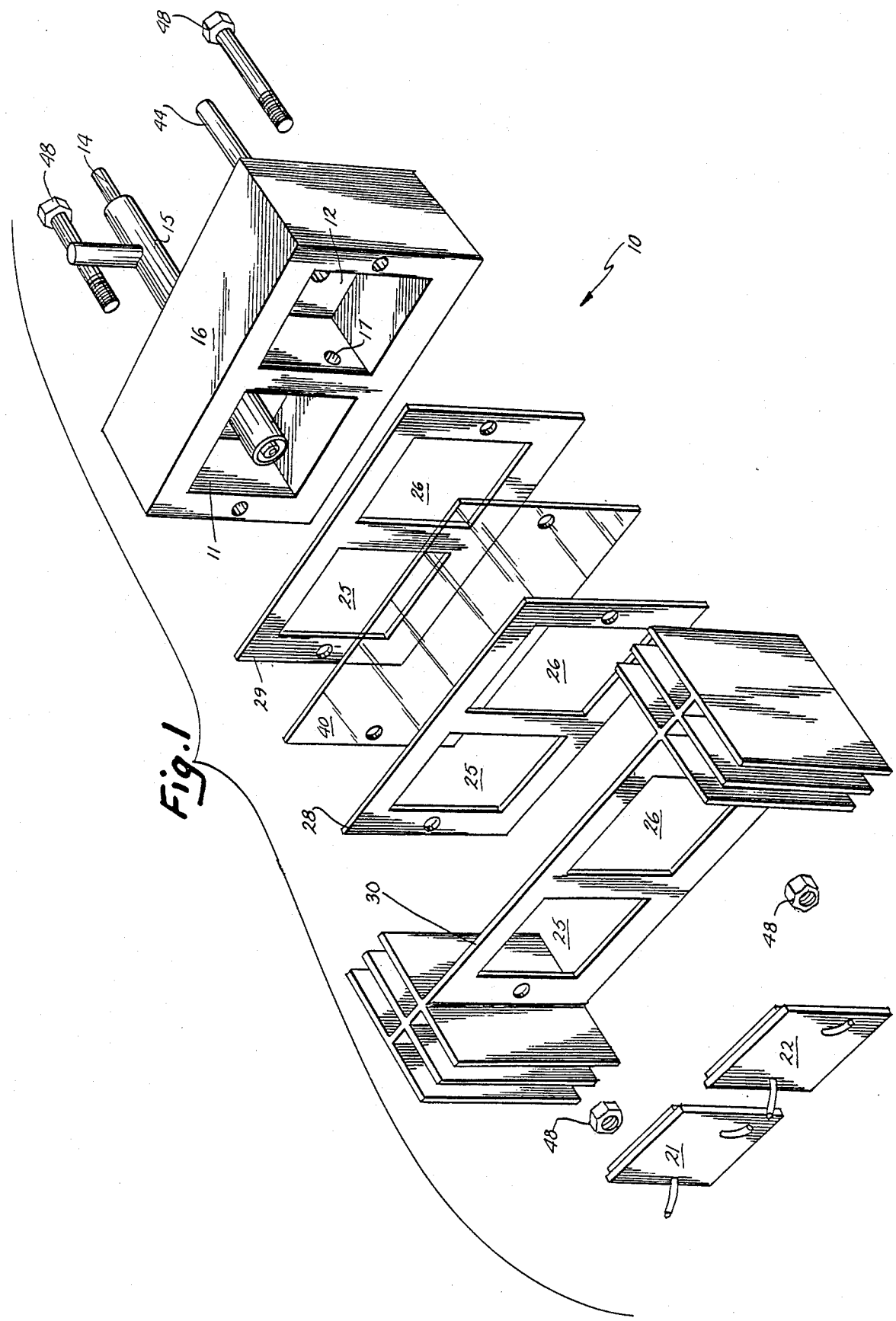
FIG. 1 is an exploded assembly of the detector of the gas analyzer of the present invention.
Figure 2:
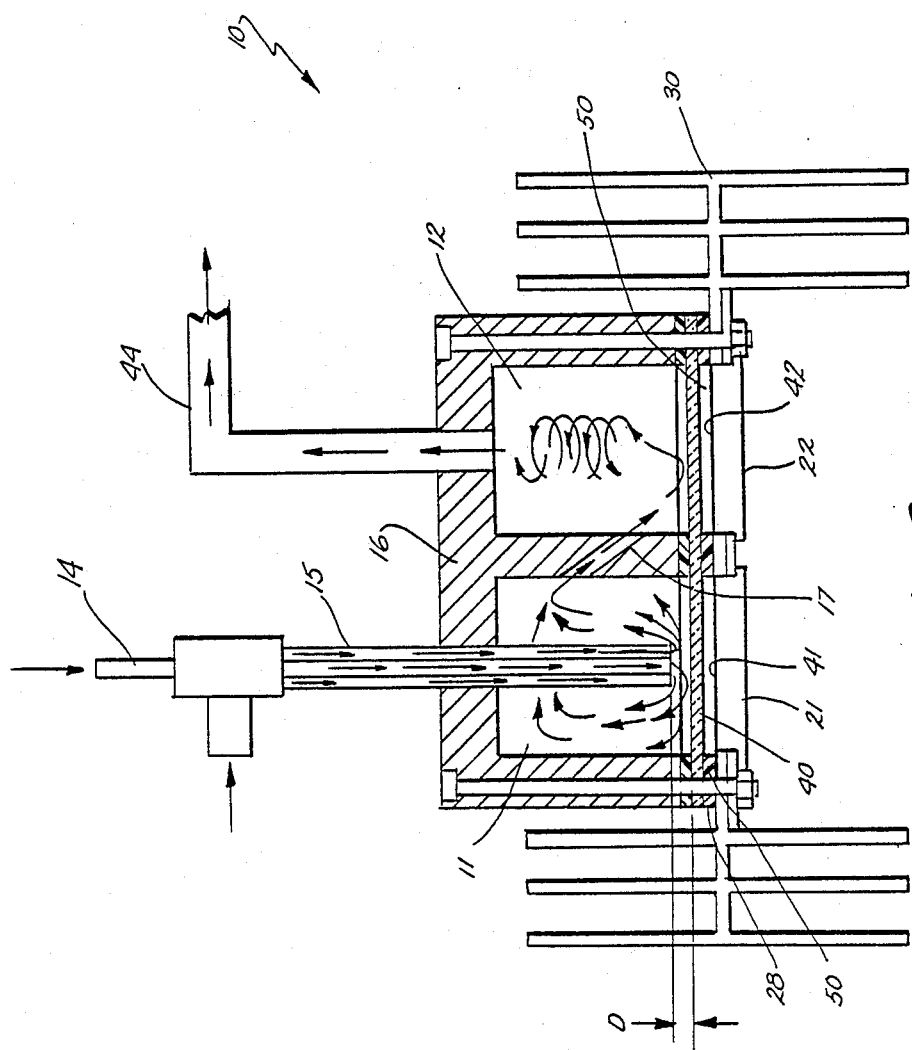
FIG. 2 is a plan view partially in section, of the detector of the present invention.

With reference now to FIGS. 1 and 2 the detector assembly of the gas analyzer of the present invention is generally illustrated at 10. The detector comprises a sample chamber 11 and a reference chamber 12. A means for delivering sample gas to the sample chamber 11 is provided comprising a first concentric tube 14 extending through the back of the sample chamber 11. The sample gas which is delivered to the sample chamber contains an oxide of nitrogen preferably nitric oxide or NO. A means for delivering ozone to the sample chamber 11 is also provided comprising a second concentric tube 15 extending through the back of the sample chamber 11. The second tube 15 provides a quantity of ozone or $O_3$ for reacting with the NO and producing a chemiluminescent reaction within the sample chamber 11. Preferably, the reference chamber 12 is disposed directly adjacent the sample chamber 11 in a common housing 16 and a means for discharging sample gas from the sample chamber 11 to the reference chamber 12 is provided comprising a cross port 17. A sample photodiode 21 is disposed immediately adjacent the sample chamber 11 for receiving light emitted from the sample chamber and producing a sample signal representative of the total photoemissivity of the sample gas disposed in the sample chamber. Similarly, a reference photodiode 22 is disposed immediately adjacent the reference chamber 12 for receiving light emitted from the reference chamber and providing a reference signal representative of both the dark current of the sample photodiode 21 and the background photoemissivity of the sample gas contained within the reference chamber. The photodiodes 21 and 22 receive light through the front face of the sample and reference chambers 11 and 12, respectively, and are mounted in windows 25 and 26 extending through gaskets 28 and 29 and heat sink 30.

Figure 7:
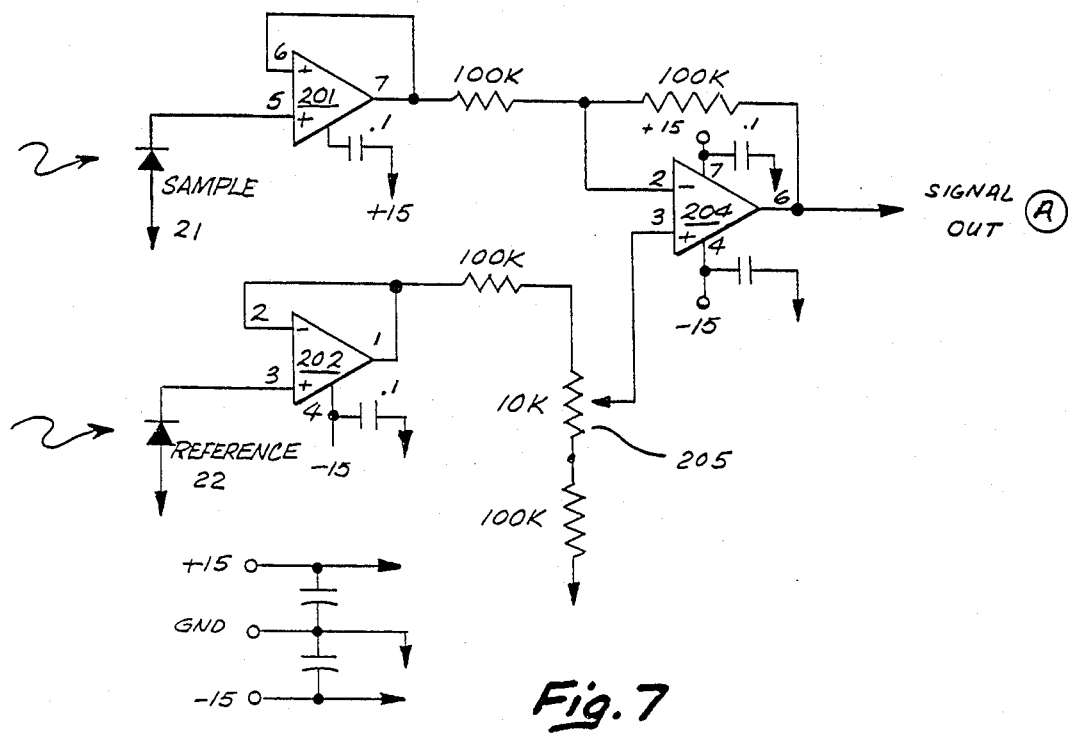
FIG. 7 is a schematic representation of a voltage following circuit and differential amplifier used to process the output of the photodiodes of the gas analyzer of the present invention.

The reference and sample photodiodes 21 and 22 are mounted in common heat sink 30 to cool the diodes and provide them with an isothermal relationship. A circuit, illustrated in FIG. 7, is provided for subtracting the output of the reference photodiode 22 from the output of the sample photodiode 21 to produce a signal representative of the concentration of NO in the sample gas compensated for detector noise or dark current and the background photoemissivity of the sample gas.

Figure 3A:
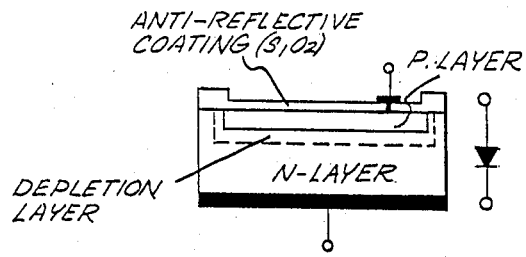
FIG. 3(a) is a sectional view of a photodiode used in the gas analyzer of the present invention.
Figure 3B:
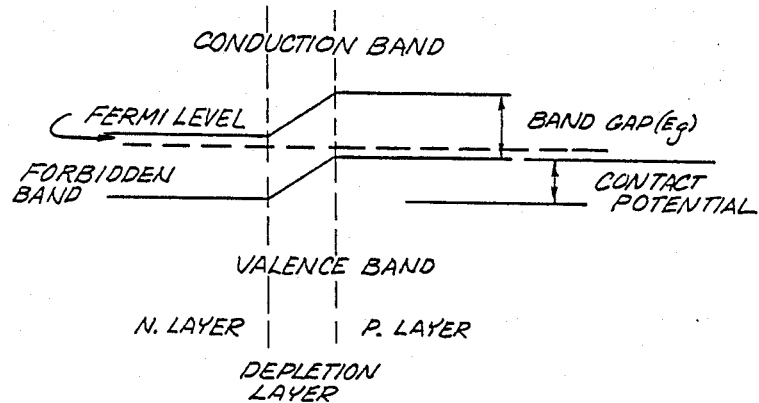
FIG. 3(b) is a condition band model of the photodiode illustrated in FIG. 3(a)

In the prior art, it was thought that photodiodes were not suitable photodetectors for monitoring a chemiluminescent reaction such as the one between NO and $O_3$ The photodiodes preferred in the present embodiment of the invention are a low capacitance, planr diffusion type known as the S1337 series of photodiodes available from the Hamamatsu Company of Japan. With reference now also to FIGS. 3(a) and 3(b), the cross section of the photodiodes is illustrated and the dark condition band model of the photodiodes is given. The low capacitance, planar diffusion type diode preferred for the present application is a high speed version of the typical planar diffusion type device which makes use of a highly pure, high resistance N-type material to enlarge the depletion layer and thereby increase the junction capacitance thus lowering response time to approximately one-tenth the normal value. The P-layer is also made thin to improve ultraviolet response Since the device is in thermal equilibrium P-layer and N-layer Fermi levels are equal and a voltage gradient develops in the depletion layer by virtue of the contact potential (potential barrier).

Figure 4:
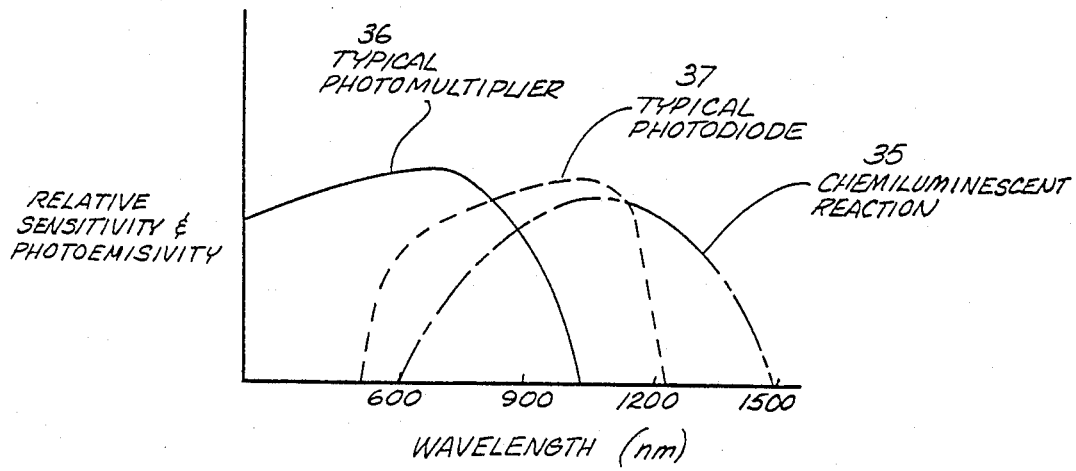
FIG. 4 is a plot of relative sensitive and photoemisivity versus wavelength for a typical photomultiplier, a typical photodiode and the chemiluminescent reaction between NO and $O_3$.

Photodiodes were thought to be unsuitable in the prior art because the output of a photodiode is at least three orders of magnitude lower than that of a typical photomultiplier. That is to say, the typical photomultiplier provides a gain approximately one thousand times that of the typical photodiode. However, with reference to FIG. 4, which is a plot of relative sensitivity and photoemissivity versus wavelength in nanometers, curve 35 illustrates that the photoemissivity of the chemiluminescent luminescent reaction of NO and $O_3$ extends from about 600 nanometers to about 1500 nanometers, while the sensitivity of the typical photomultiplier illustrated by curve 36 drops off significantly above 900 nanometers. On the other hand the sensitivity of the typical photodiode, illustrated at 37, starts just below 600 nanometers and extends beyond 1200 nanometers. While the sensitivities plotted in FIG. 4 are not representative of true output since the output of the typical photomultiplier is three orders of magnitude higher than the output of the typical photodiode, this plot of relative sensitivities is significant since it shows that the typical photodiode plotted at 37 has a sensitivity that more closely matches the photoemissivity of the chemiluminescent reaction plotted at 35 than that of the typical photomultiplier plotted at 36. However, it has never been thought possible to use photodiodes in this application before because of their low output and high dark current. Stated otherwise, the typical photodiode provides a low output and a poor signal to noise ratio. Nevertheless, according to the present invention, these problems are solved by providing two photodiodes in an isothermal relationship. A sample photodiode is provided for monitoring the total photoemissivity of the sample gas, including that due to chemiluminescence and a reference photodiode is provided to measure the background photoemissivity of the sample gas, as well as the dark current in the photodiodes. Operation of the photodiode pair in this manner provides good common mode rejection and a much improved signal to noise ratio. Also, as will hereinafter be described, good sample chamber design places the planar light sensitive surface of the photodiodes directly adjacent a planar chemiluminescent display which enhances sensitivity and the provision of high impedance, low leakage current voltage following circuits enables the processing circuit to "see" the low output of the photodiodes.

With specific reference again to FIGS. 1 and 2, it is illustrated that sample gas and ozone are delivered to the sample-chamber 11 through concentric inner and outer tubes 14 and 15 which extend in a direction generally perpendicular to a glass window 40 which forms the front of the sample chamber 11. The concentric inner and outer tubes 14 and 15 terminate or are provided with ends which nearly abut the inside surface of the window 40. In fact, the ends of the concentric tubes 14 and 15 are separated from the inside surface of the window 40 by a distance D of approximately 0.020 inches. This arrangement and this separation distance is important to the operation of the detector since, as best illustrated by the arrows disposed within th sample cell 11 in FIG. 2, ozone and sample gas containing NO are sprayed directly on the inside surface of the glass window 40 by this arrangement to provide a planar and generally circular area of chemiluminescence which is directed on the inside surface of the glass 40. This area of chemiluminescence is thus positioned directly adjacent and parallel to the planar photosensitive surface 41 of the sample detector 21. Since the photons emitted by the chemiluminescent reaction are very dispersive, this insures the best possible response from the sample photodiode 21 and, in fact, results in a configuration much better than that possible with the typical prior art photomultiplier where it was difficult to position the detector plates of the photomultiplier directly adjacent the area of chemiluminesence because of the physical dimensions of the evacuated glass envelope within which the detector plates are enclosed.

Since the chemiluminescent reaction taking place within the sample chamber 11 is practically instantaneous, (on the order of 10 milliseconds) by the time the sample gas is discharged into the reference chamber 12 through the cross port 17, (at a typical sample flow of 2 liters/minute) the chemiluminescent reaction is terminated. The cross port 17 is provided with an angular orientation relative to the front of the sample chamber 11 and the reference chamber 12 so that light generated in the front of the sample chamber 11 from the chemiluminescent reaction does not have a clear path to the photosensitive surface 42 of the reference diode 22. Still further, the angular orientation of the cross port 17 directs the sample gas exhausted from the reference cell 11 to the inside surface of the glass window 40 of reference cell 12. Because the reference and sample photodiodes are disposed in an isothermal relationship on common heat sink 30, the reference photodiode provides an accurate measure of the dark current within the sample photodiode. However, also important to the design of the detector assembly is the fact that the reference photodicde 22 provides a measure of the background photoemissivity of the sample gas. It should be appreciated that this is important in cases where the analyzer is used to monitor the hot exhaust gas of an internal combustion engine since such an exhaust gas stream will contain hot photoemissive particles which will add to the total output of the photodetector and in effect degrade the signal to noise ratio of the instrument. However, the reference chamber 12 and reference photodiode 22 of the present invention provide an accurate measure of this background photoemissivity and provide a technique for subtracting the same from the output of the sample photodiode which contains a signal representative of the photoemissivity of the chemiluminescent reaction taking place in the detector This is another feature considered important in the construction of a chemiluminescent oxides of nitrogen gas analyzer employing photodiodes. After a suitable residence time within the reference chamber 12, the sample gas is exhausted through line 44, extending from the back of the sample chamber 12.

As best illustrated in FIG. 1, the detector assembly comprises an aluminum housing 16 within which the sample and reference cells 11 and 12 are formed. The surfaces of the cells 11 and 12 may be painted or otherwise suitably coated with a reflective material for directing the output of the photoemissive gases contained therein toward the glass window 40 which forms the front surface of the cells. Manufacture of the cells in a common block 16 is preferred since it is desirable to minimize any temperature differential between the sample cell 11 and the reference cell 12. The tubes 14, 15 and 44 are threadably secured or otherwise suitably secured in the back of the aluminum block 16. The glass window 40 is secured to the front face of the detector housing or block 16 between Viton gaskets 28 and 29 and heat sink 30. Heat sink 30 is suitably clamped to the housing 16 with fasteners 48 or the like. Viton is a trademark of the E. I. Dupont Demour Company and identifies a fluorocarbon, elastomer material which is opaque, heat insulative and highly resistant to corrosion. These characteristics are important to the design of the detector assembly since all ambient light must be excluded from the reference and detector cells, the sample gas may be quite hot and the corrosive effects of ozone can destroy other gasket materials.

With particular reference now to FIG. 2, it is also illustrated that the gasket 28 disposed between the glass window 40 and the heat sink 30, is used to establish a small air gap 50 between the outside surface of the glass 40 and the photodiodes 21 and 22. This air gap is considered important to thermally isolate the photodiodes 21 and 22 from the hot sample gas contained within the reference and sample chambers. This, combined with the heat sink 30, lowers the operating temperature of the photodiodes 21 and 22. This is important, since heat has a deleterious effect on the operation and life of the photodiodes. It should be readily appreciated that the application of photodiodes to a gas analyzer detector of the present type is a significant advance in the art since these diodes are relatively tough, impact resistant devices which are extremely inexpensive when compared to the typical vacuum tube type photomultiplier and which provide minimal cooling, light shielding and RF shielding requirements when compared to the typical photomultiplier. Still further, the photodiodes may be physically oriented relative to the photoemissive chemiluminescent display to enhance the output of the detector.

Figure 5:
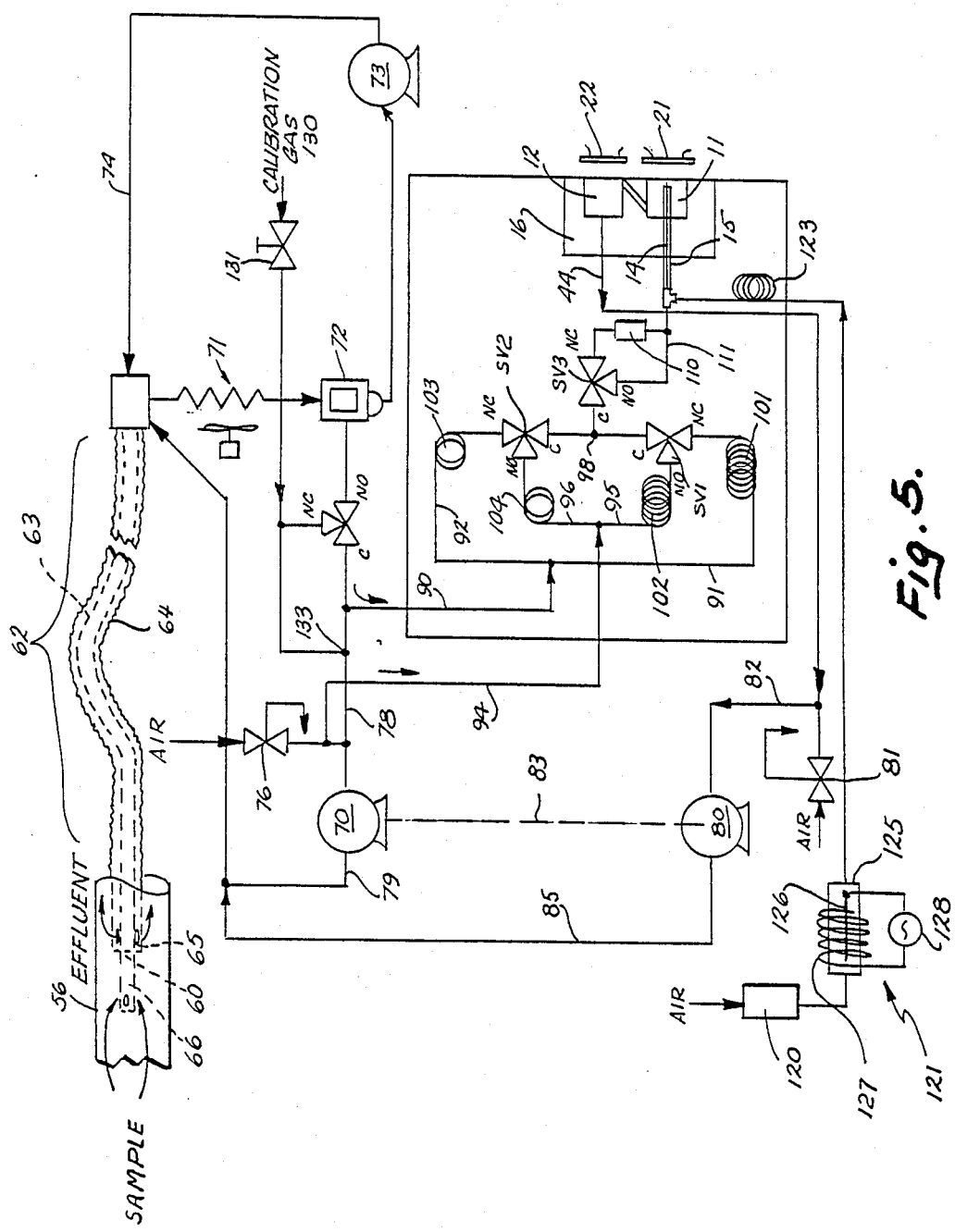
FIG. 5 is a functional diagram of an embodiment of the gas analyzer of the present invention wherein dilution of the sample takes place in the gas analyzer.

With reference now to FIG. 5, a functional diagram of the oxides of nitrogen gas analyzer of the present invention is generally illustrated at 55. In this case, an auto gas analyzer is illustrated, the tail pipe of the combustion engine of the automotive vehicle being schematically illustrated at 56. With respect to the previous description, like components are given the same numeral designation and the sample cell housing is illustrated at 16, the sample cell is at 11, and the reference cell is at 12. The lines 14 and 15 are illustrated-entering the back of the sample cell 11 while the exhaust line 44 is illustrated leaving the back of the reference cell 12. The sample photodiode is illustrated at 21 and the reference photodiode is illustrated at 22. The analyzer includes a sample probe 60 which is adapted for placement within the exhaust pipe 56 of the combustion engine. In the case of an auto gas analyzer, the exhaust gas is often quite hot. Thus, the first concern relates to the cooling of the sample drawn from the exhaust pipe 56 According to the present invention, the hot sample gas drawn from the sample probe 60 passes through a line heat exchanger 62 comprising a pair of inner and outer concentric flexible lines 63 and 64. Generally, the flexible lines 63 and 64 are approximately 20 feet long and are formed from a flexible Teflon, polymeric material which is capable of withstanding relatively high temperatures: The effluent from the analyzer 55 is pumped back into the tail pipe 56 through the outer tube 64 in a counterflow fashion, against the sample which is drawn from the exhaust pipe 56 through the centerline 63. This, in effect, forms a counterflow line heat exchanger which sufficiently lowers the temperature of the sample gas to permit the use of flexible polymeric materials for the line 62 which interconnects the sample probe and the analyzer This, of course, greatly facilitates the use of the analyzer, permitting flexibility in the placement of the tail pipe mounted sample probe and lowering the cost of the flexible connection extending between the tail pipe and the analyzer. The effluent from the analyzer which is pumped back to the tail pipe 56 through the outer flexible line 64 exits the sample probe 60 at a point 65 which is downstream from the inlet 66 of the sample probe.

A sample pump head disposed at 70 draws sample gas from the sample probe 60 through interior line 63 of line heat exchanger 62 to a stainless steel heat exchanger 71 The heat exchanger schematically illustrated at 71, comprises a length of stainless steel tubing having fins extending from the surface thereof which are cooled by a fan disposed within the analyzer housing. Since the exhaust gas from an internal combustion engine contains large amounts of water vapor, the gas leaving the heat exchanger 71 is normally saturated and contains a considerable amount of condensate. Thus, the sample exiting heat exchanger 71 is inputted to a low volume filter bowl and water trap at 72. The filter bowl and water trap 72 contains a sintered Teflon filter media which removes particulate material from the sample flow and the fluid collecting bowl on the bottom of the filter housing is pumped clear by a slow moving peristaltic pump 73. The peristaltic pump 73 returns the condensate via line 74 to the exterior line 64 of the line heat exchanger 62 for discharge with the effluent from the analyzer at 65 on sample probe 60.

The pressure of the sample pump head 70 is regulated by a sample regulator valve 76 which is disposed just upstream from the sample pump head 70 for introducing a predetermined amount of air to the sample pump head 70 and establishing a predetermined sample gas pressure. For example, in the present embodiment of the invention, the sample regulator valve 76 is normally adjusted to provide a sample gas pressure on line 78 of approximately 5 inches of mercury. The sample pump head 70 and sample regulator valve 76 thus determine the pressure at which sample gas is drawn from tailpipe 56 and in effect determine the delivery pressure of sample to the sample chamber 11. The output of the sample pump head 70, which contains a mixture of ambient air and cooled sample gas is directed via line 79 back to the exterior tube of line heat exchanger 62 for discharge with the remainder of the effluent of the analyzer at 65 on sample probe 60.

The analyzer further comprises an effluent pump head 80 for drawing effluent from reference chamber 12 and a effluent regulator valve is disposed at 81 for introducing air to the effluent pump head 80 and thus establishing a predetermined effluent gas pressure In this case, the effluent regulator valve 81 is adjusted to provide an effluent gas pressure of approximately 8 inches of mercury in line 82. The output of effluent pump head 80, which comprises a mixture of cooled sample gas and air is directed via line 85 back to the exterior line 64 of line heat exchanger 62 for discharge with the remainder of the effluent of the gas analyzer at the sample prcbe 60. As schematically illustrated by the line 83, the pump heads 70 and 80 may be driven by a common motor. The total amount of sample gas drawn from the tailpipe 56 of the engine is approximately five liters per minute. A mixture of cooled sample gas and air is pumped back into the sample probe 60 through line heat exchanger 62 at a rate of apprpoximately 15 liters per minute Thus, the heat exchange capability of the concentric line heat exchanger 62 is substantial.

The sample gas drawn frcm an intornal combustion engine normally contains significant amounts of carbon dioxide $CO_2$ which has a quenching effect on the chemiluminescent reaction of NO and $O_3$. Also, after cooling the sample gas is normally saturated with water so that condensate in the analyzer is a constant problem. Thus according to the present invention, these and other problems in the prior art are solved by providing an arrangement for introducing dilution air into the sample gas prior to delivery of the sample gas to the sample chamber 11. In the present case, a dilution ratio of air to sample gas of approximately 9:1 or a turndcwn of approximately 9:1 is preferred. In addition to substantially eliminating problems with quenching and condensate, dilution ratios of 9:1 provide an analyzer with greater range and reduce ozone requirements. The latter is particularly important because ozone is itself a noxious gas.

In the embodiment of FIG. 5, dilution or turndown is accomplished with a viscous metering technique. More particularly, sample gas at the sample gas pressure determined by sample regulator valve 76 is delivered to the normally closed ports of first and second dilution solenoid valves SV1 and SV2 via lines 90, 91 and 92. Similarly, dilution air at the sample gas pressure is delivered from regulator valve 76 via lines 94, 95 and 96 to the normally open ports of first and second dilution solenoid valves SV1 and SV2. Both the valves SV1 and SV2 are provided with a normally open port, a normally closed port and a common port. The common ports are connected together at 98 and form an output which is directed to the sample chamber 11. The first dilution valve SV1 is provided with first and second flow resistances 101 and 102, which are connected to the normally closed port and normally open port, respectively, of valve SV1. The first and second flow resistances 101 and 102 are provided with a first predetermined flow resistance value. Similarly, the normally closed port and normally open port of valve SV2 are provided with third and fourth flow resistances 103 and 104, respectively. The third and fourth flow resistances 103 and 104 are provided with a second predetermined flow resistance value. The flow resistances 101 through 104 each comprise a capillary tube type of flow resistance which provide a viscous metering effect. In such devices, the flow therethrough is determined by the diametcr of thc capillary and its length. The flow resistances 101 and 102 are sized to permit a total flow of approximately 1800 cubic centimeters (cc's) per minute. The third and fourth flow resistances 103 and 104 are sized to permit a total flow of approximately 200 cc's per minute. Thus, when sample gas flow through either of the third or fourth flow resistances 103 or 104 is mixed with dilution air flow through either one of the first and second flow resistances 101 and 102 at common point 98, between solenoid valves SV1 and SV2, a turndown or dilution ratio of approximately 9:1 is achieved. Within certain viscosity limits, the effects of which are negligible in this case, this turndown ratio is constant and is determined by the dimensions of flow resistances 101 through 104.

The dilution solenoid valves SV1 and SV2 are operated to provide a zero condition in the analyzer when neither of the dilution valves are actuated and only air is supplied to comon point 98 through the flow resistances 102 and 104 and the normally open ports of valves SV1 and SV2. A low range for the analyzer is established when both of the dilution valves SV1 and SV2 are actuated and only sample gas is supplied to the common point 98 disposed therebetween from flow resistances 101 and 103 connected o the normally closed ports of valves SV1 and SV2. A high range is established for the analyzer when only one of the dilution valves SV1 and SV2 is actuated, such as the valve SV2 inputting approximately 1800 cc's per minute of dilution air to common point 98 through flow resistance 104 and inputting approximately 200 cc's of sample gas to common point 98 through the normally open port of valve SV1 and flow resistance 102.

In the case of a gasoline engine, most of the $NO_x$ generated by the engine is NO, which readily combines with ozone to create a measurable chemiluminescent reaction. However, in the presence of oxygen, the NO slowly oxidizes to $NO_2$. In other types of internal combustion engines such as diesel engines where air/fuel ratios are lower and the engines operate at higher compression ratios and temperatures, a certain percentage of $NO_2$ is formed directly in the combustion process. In the present analyzer it is possible to simply measure the existing NO in the sample and then infer the $NO_2$ content knowing the residence time of the sample within the analyzer and/or the expected percentage of $NO_2$ output of the engine which, in the case of a diesel engine, is approximately 10 percent of the total $NO_x$ output. However, where it is desirable to provide a direct measure of total $NO_x$ rather than discrete NO, a heated molebdemum or stainless steel gauze catalyst chamber is provided at 110. The catalyst contained within the chamber 110 is heated to an elevated temperature of approximately 600 degrees Celsius. and in this environment, $NO_2$ is reduced to NO. To facilitate this process, the common point 98 between dilution solenoid valves SV1 and SV2 is connected to the common port of a third solenoid valve or divertor valve SV3. The normally open port of valve SV3 is connected to line 111 which leads to the interior tube 14 of the concentric tube arrangement injecting sample gas to the sample chamber 11. The normally closed port of valve SV3 is connected to the catalyst chamber 110, whereby upon actuation of the solenoid valve SV3, sample gas is diverted through the catalyst chamber 110 to reduce any $NO_2$ in the sample gas stream to NO so that the chemiluminescent reaction taking place in sample gas chamber 11 is representative of the total $NO_x$ in the sample. By switching the mode of the analyzer from discrete NO and total $NO_x$ with the divertor valve SV3, an accurate measure of $NO_2$ can be obtained by subtracting the concentration of NO from the concentration of $NO_x$. Normally this is accomplished with software in a microprocessor which drives the analyzer display.

Ozone for the chemiluminescent reaction in sample chamber 11 is supplied through a silica gel drier 120, ozone generator 121 and an ozone capillary type flow resistance 123. Ozone is generated in the ozone generator 121 via a corona discharge created by a pair of electrodes across which an AC voltage is applied. In this case, a glass tube 125 is provided having a central electrode 126 extending therethrough and an exterior electrode 127 deposited, wound or otherwise suitably formed on the exterior of the glass tube. A suitable source of AC voltage 128 is impressed across the electrodes 126 and 127. Air is drawn axially through the glass tube 125 by the reduced pressure within sample chamber 11. Silica gel drier 120 is provided for reducing the humidity of the air entering the ozone generator 121 since high humidity can inhibit the corona discharged and the formation of ozone. The capillary flow resistance 123 is sized so as to provide a somewhat greater than stoichiometric concentration of ozone to the chemiluminescent reaction taking place in the sample chamber 11. As previously noted, the provision of a turndown of 9:1 has two additional beneficial effects on the operation of the analyzer, one of which is the provision of an analyzer having extending range, the other of which is a ten-fold reduction in ozone requirements which is important, since ozone is itself a noxious gas.

The gas analyzer further comprises a calibration solenoid valve SV4 disposed between the filter bowl 72 and the line 90 which supplies sample gas to the dilution valves SV1 and SV2 The calibration valve SV4 includes a normally open port, which is connected to filter 72 and a common port which is connected to line 90. The normally closed port of valve SV4 is connected to a source of calibration gas at 130 through control valve 131. The normally closed port of valve SV4 is also connected to a T-point 133 on line 78, which is regulated to the sample gas pressure by sample regulator valve 76 so that when the valve SV4 is actuated, the calibration gas, having a known predetermined quantity of NO, is supplied through valve SV4 at the sample gas pressure determined by regulator valve 76.

Figure 6:
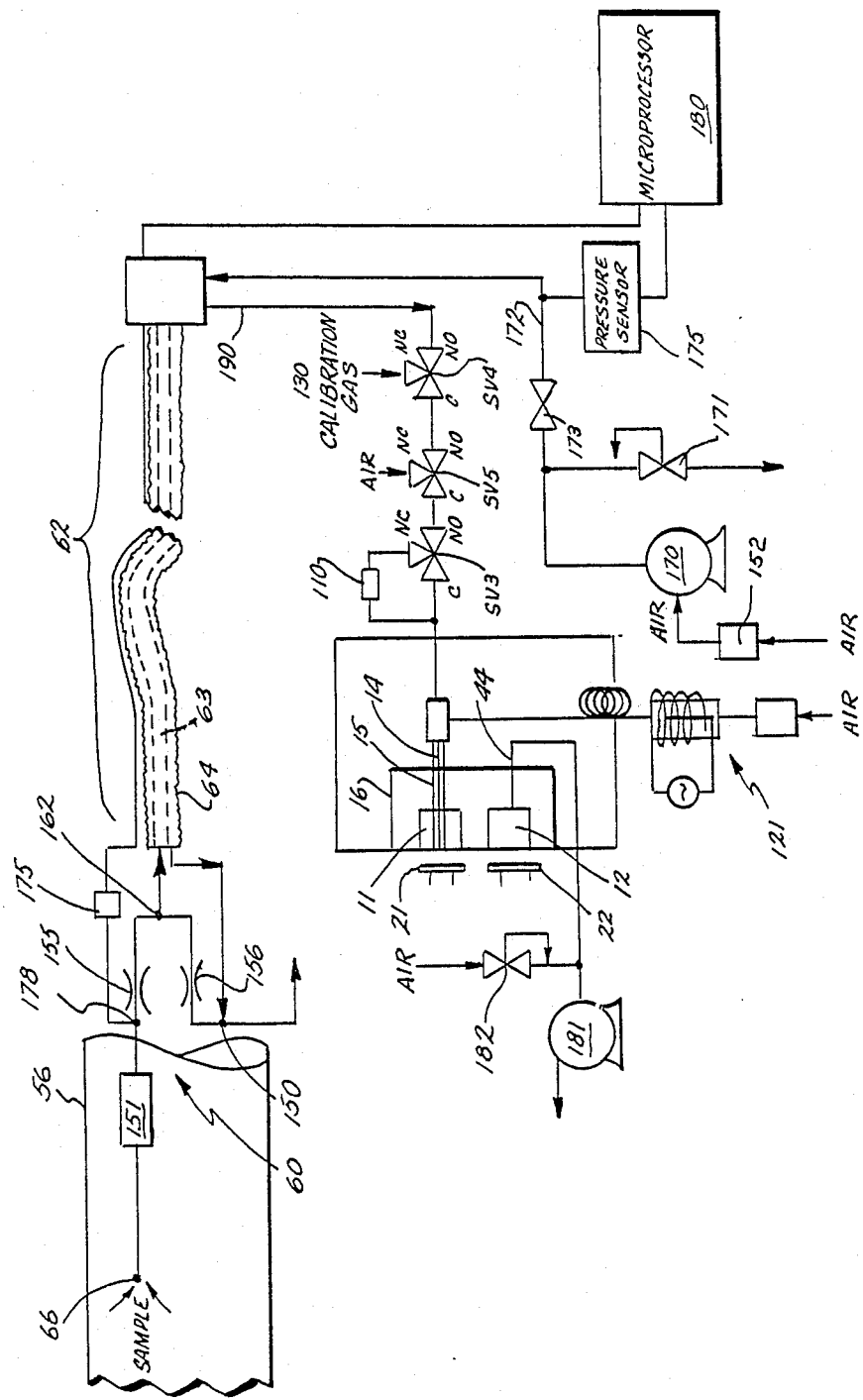
FIG. 6 is a functional diagram of another embodiment of the gas analyzer of the present invention wherein dilution of the sample gas takes place in the tailpipe of an automotive vehicle.

With reference now to FIG. 6, another embodiment of the gas analyzer of the present invention is illustrated wherein dilution of the sample gas takes place in the tailpipe 56 of the vehicle. As previously discussed, dilution is considered important to reduce $CO_2$ quenching, to extend the range of the instrument, to reduce ozone requirements and to reduce problems with condensate in the analyzer. In the embodiment of FIG. 6, dilution air is pumped into the sample probe 60 where it is introduced to the sample flow with a sonic metering technique. Many components in this embodiment are similar to those in the embodiment of FIG. 5 and like components are given the same numeral designation. In this embodiment of the invention, the line heat exchanger 62 comprises inner and outer concentric, flexible Teflon lines 63 and 64 as before. However, in this case, the outer line 64 carries dilution air rather than effluent from the analyzer. Dilution air is pumped to a point 150 on sample probe 60 where it is discharged to the atmosphere adjacent to the tailpipe 56. The point 150 on sample probe 60 is downstream of the point 66 on sample probe 60 (which is preferably inside the tailpipe 56) where sample gas or exhaust gas is drawn into the sample probe The sample probe 60 includes a filter 151 for filtering particulate matter from the sample gas flow. Flow from the filter 151 is then directed to a sample sonic orifice 155 while dilution air from point 150 is directed to a dilution air sonic orifice 156. The orifices 155 and 156 are sized such that the pressure drop across the orifices is on the order of 15 inches of mercury or more so that sonic flow is achieved in both orifices. With sonic flow conditions in an orifice, fluctuations in downstream pressure will not effect the mass flow rate through the . orifice. Within practical limits, only an increase in upstream pressure will incrcase the flow through the orifice. The upstream pressure on the sample sonic orifice 155 is the resultant of the exhaust gas pressure and the pressure drop through the filter 151. The upstream pressure on the dilution air sonic orifice is atmospheric pressure and is regarded to be a constant. The sample sonic orifice 155 and the dilution air orifice 156 are small, sapphire orifices which are provided with diameters which are proportionate to and determine the diuution ratio of air to sample gas. The flow from the sample gas orifice 155 and the dilution air orifice 156 are combined at common point 162 which discharges the diluted sample gas flow to the interior line 63 of line heat exchanger 62. Dilution of the sample gas in the tailpipe eliminates much of the complexity and cost of the embodiment of the invention illustrated in FIG. 5 in that components such as stainless steel heat exchanger 71, filter bowl and water trap 72, condensate pump 73, dilution valves SV1 and SV2, etc., are eliminated.

Dilution air is supplied to the outer concentric line 64 of line heat exchanger 62 by a simple aquarium type dilution pump 170 which draws atmospheric air through a filter 152. The output of the pump 170 is regulated by a back pressure dilution regulator valve 171. The output of the dilution pump 170 is directed to the line heat exchanger 62 via line 172, which includes a control valve 173. Since the dilution air is exhausted to the atmosphere at point 150, dilution air is supplied to the dilution air orifice at essentially atmospheric pressure. This is regarded as a constant. A pressure sensor 175 is required to provide a measure of the exhaust gas pressure at a point 178 upstream of the sonic orifice 155. Signals from the pressure transducer 175 are inputted to a microprocessor 180 which includes a lookup table or a curve fit for modifying the actual dilution ratio and flow as it is affected by changes in the pressure of the exhaust gas.

Diluted sample gas is drawn through the interior tube 63 of line heat exchanger 62 and into the analyzer by a sample pump 181. The sample gas pressure is determined by a regulator valve 182 disposed on the input of sample pump 181. In this case, the output of sample pump 181 is simply discharged to the atmosphere. As in the previous embodiment of the invention, diluted sample gas is drawn through a divertor valve SV3 which, when energized, directs diluted sample flow through catalyst chamber 110 for reducing any $NO_2$ in the sample gas. Diluted sample gas also flows through first calibration valve SV4. The first calibration valve SV4 includes a normally open port connected to the line heat exchanger via line 190. The common port of valve SV4 directs sample to a second calibration valve SV5. The normally closed port of first calibration valve SV4 is connected to a source of calibration gas 130. When the first calibration valve SV4 is actuated, a source of sample gas having a known concentration of NO is inputted to the sample chamber 11. The second calibration valve SV5 includes a normally open port which is connected to the common port of first calibration valve SV4 for receiving sample flow therethrough. The common port of second calibration valve SV5 is connected to the normally open port of divertor valve SV3. The normally closed port of second calibration valve SV5 is connected to a source of air so that when the second calibration valve SV5 is energized, pure air is inputted to the sample chamber 11 to zero the analyzer.

The viscous metering technique illustrated in FIG. 5 and the sonic metering technique illustrated in FIG. 6 produce another important feature of the gas analyzer of the present invention. In both cases, these metering techniques provide a means for insuring a constant flow of sample gas through the instrument which is of course important because the intensity of the chemiluminescent reaction which is monitored is affected by flow rates.

Figure 8:
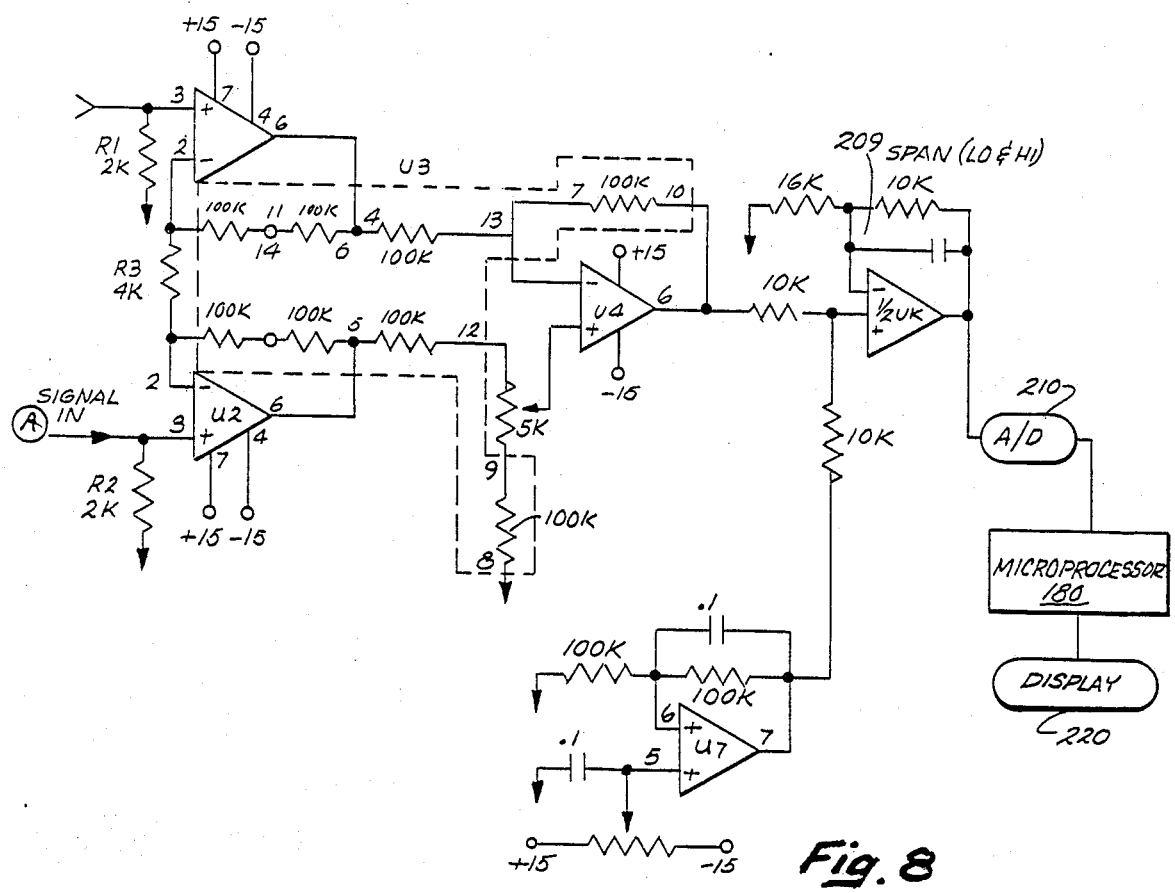
FIG. 8 is a schematic of an instrumentation amplifier, and zero and span adjustment circuit used to process the output of the photodiodes of the gas analyzer of the present invention and input the same to a microprocessor controlled display.

With reference now to FIG. 7, a circuit for processing the output of the sample photodetector and the reference photodetector is schematically illustrated. The circuit of FIG. 7 is considered a preamplification circuit which is normally mounted directly adjacent the heat sink 30 and photodiodes 21 and 22. The sample and reference diodes 21 and 22 are operated in a reverse bias configuration. The output of the sample and reference photodiodes are inputted to unity gain voltage following amplifiers 201 and 202, respectively. The voltage followers 201 and 202 are mounted in a common package and preferably comprise a National Semiconductor LF412CN integrated circuit having an industrial temperature range. This voltage following circuit is desirable because it has field effect transistor (FET) inputs which have very high impedances and very low leakage currents which do little to color the reaction of the photodiodes. It is preferable to employ voltage following circuits 201 and 202 on a common integrated circuit to insure that the operating conditions of both circuits are identical. This insures good common mode rejection. Power to this circuit is plus and minus 15 volts DC where indicated. The outputs of voltage following circuits 201 and 202 are inputted to a unity gain differential amplifier 204. Preferably, the differential amplifier 204 is a National Semiconductor LM11CN integrated circuit connected to a plus 15 volt and minus 15 volt DC power supply, as indicated. Also, it is preferable that the differential amplifier 204 have FET inputs. The output of the differential amplifier 204 is representative of the output of sample photodiode 21 minus the output of reference photodiode 22. The sample photodiode 21 provides an output representative of the photoemissivity of any chemiluminescent reaction, the background photoemissivity of the sample gas, as well as noise or a dark current. The reference photodiode provides a signal representative of the background photoemissivity of the sample gas and the dark current. A potentiometer at 205 is provided between the output of the reference voltage follower 202 and the differential amplifier 204 for adjusting the common mode rejection ratio of this circuit Although the output of the preamplifier of FIG. 7 could be inputted directly to an analog to digital (A/D) converter, and then to a microprocessor, in the preferred embodiment of the invention the output of FIG. 7 is inputted to an amplification and zero offsetting circuit illustrated in FIG. 8. The output of FIG. 7 is first inputted to a typical instrumentation amplifier comprising the three operational amplifiers U1, U2 and U4. More particularly, the output of FIG. 7 is inputted on pin 3 of operational amplifier U2 or the noninverting input of the instrumentation amplifier. The inverting input to the instrumentation amplifier or pin 3 of U1 is connected to ground and is left floating. This may provide some noise rejection capability. The instrumentation amplifier comprising operational amplifiers U1, U2 and U4 preferably comprise a National Semiconductor LM11CN integrated circuit having a gain of approximately 4000.

The output of the instrumentation amplifier is inputted to an offset amplifier U5. The offset amplifier U5 is a variable gain amplifier which can be adjusted with a span potentiometer 209 in the feedback loop of the amplifier. A zero offset value is also inputted to amplifier U5 from a zero offset amplifier U7. The amplifier U7 is a noninverting amplifier with a gain of two which adds a constant to the output of the instrumentation amplifier to determine zero. When a calibrated gas is inputted to the instrument, a span adjustment is similarly accomplished with the span potentiometer in the feedback loop of the offset amplifier U5. The output of the offset amplifier U5 is inputted to an A/D converter 210 and then to a microprocessor 180 which drives a display 220. The microprocessor 180 may include software which calculates inferred $NO_2$ quantities from discrete measurements of NO and $NO_x$ may include curve fitting software to further compensate for temperature and pressure.

Figure 9:
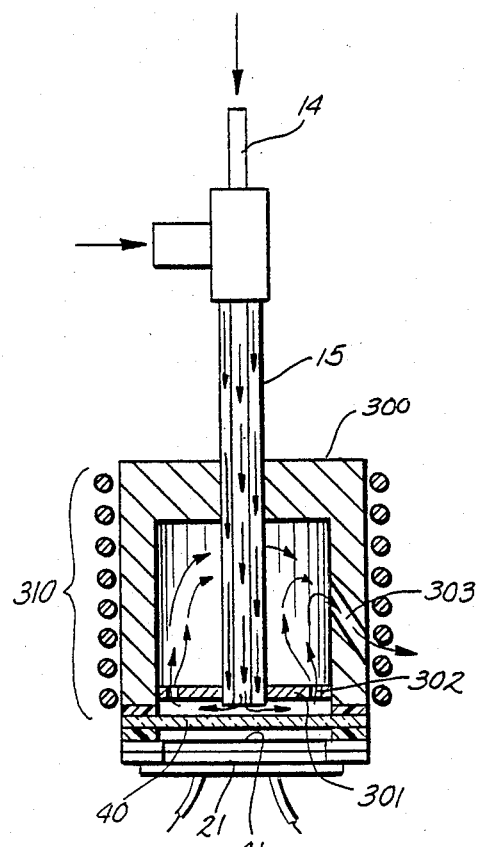
FIG. 9 is a plan view partially in section of another embodiment of the detector of the present invention.
Figure 10:
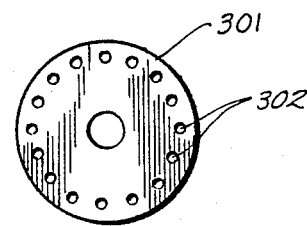
FIG. 10 is a plan view of a baffle provided in the detector of FIG. 10.

With reference now to FIG. 9, still another embodiment of the invention is illustrated. FIG. 9 illustrates an embodiment of the invention wherein a single sample photodiode is used to measure the output of the chemiluminescent reaction. In this case, a single sample cell 300 is provided with concentric sample and ozone tubes 14 and 15, respectively, extending therethrough with a planar, transparent window 40 extending across the front thereof. A single sample photodiode 21 is disposed adjacent to and directly in front of the transparent sample window 40 with the planar, light-sensitive surface 41 of the sample photodiode 21 adjacent to and parallel to the surface of the planar sample window 40. The single sample cell 300 illustrated in FIG. 9 embodies the number of improvements which are applicable both to single and dual photodiode systems. In particular, the sample cell 300 includes a baffle 301 for insuring that the ozone and sample gas impinging the inside of the sample window 40 is retained against the inside surface of the sample window 40 for a predetermined period. The baffle 301 surrounds the concentric sample and ozone tubes 14 and 15, respectively, and is effectively sealed thereto so that sample gas and ozone are channeled from the centrally located tubes 14 and 15 along the inside surface of the sample window 40 to a peripheral array of apertures 302, best illustrated in FIG. 10. This insures that the chemiluminescent reaction takes place directly adjacent the planar, light-sensitive surface 41 of the sample photodiode 21, thus enhancing the possibility that the photodiode 21 will capture the photons emitted in the chemiluminescent reaction. The gas exiting the annular array of ports at 302 is channeled out of the sample chamber 300, for example, by an exit port 303. The provision of baffle 301 is found to significantly improve the output and linearity of the device, thus significantly lessening the need for the second reference photodiode found in earlier embodiments. However, it should be appreciated that the baffle 301 is equally suitable to those earlier embodiments where dual sample ad reference photodetectors are provided. In the case of a dual photodetector system, the baffle 301 is provided only on the sample photodiode.

The detector illustrated in FIG. 9 also features an arrangement for holding the sample photodiode at a constant temperature. This is most conveniently accomplished by applying a heating coil, schematically illustrated at 310, which encompasses the sample cell 300 and sample photodiode 21. While there are other techniques for holding the sample cell and the sample photodiode at a constant temperature, the provision of heating coil 310 is thought to be the most expedient fashion. While the heating of the sample photodiode 21 decreases its output, the maintenance of the sample photodiode at a constant temperature stabilizes the output span of the photodetector and greatly enhances the accuracy of the device. This feature is thought to be most important in the operation of a detector employing a single sample photodiode 21. However, the addition of the heating coil 310 is equally applicable to those early embodiments employing dual sample and reference photodiodes. In the application of this concept to earlier embodiments, the heating coil 310 would encompass both the sample and reference cells as well as the sample and reference photodiodes for holding the temperature of the same constant and thus stabilizing the output span of the device.

Figure 11:
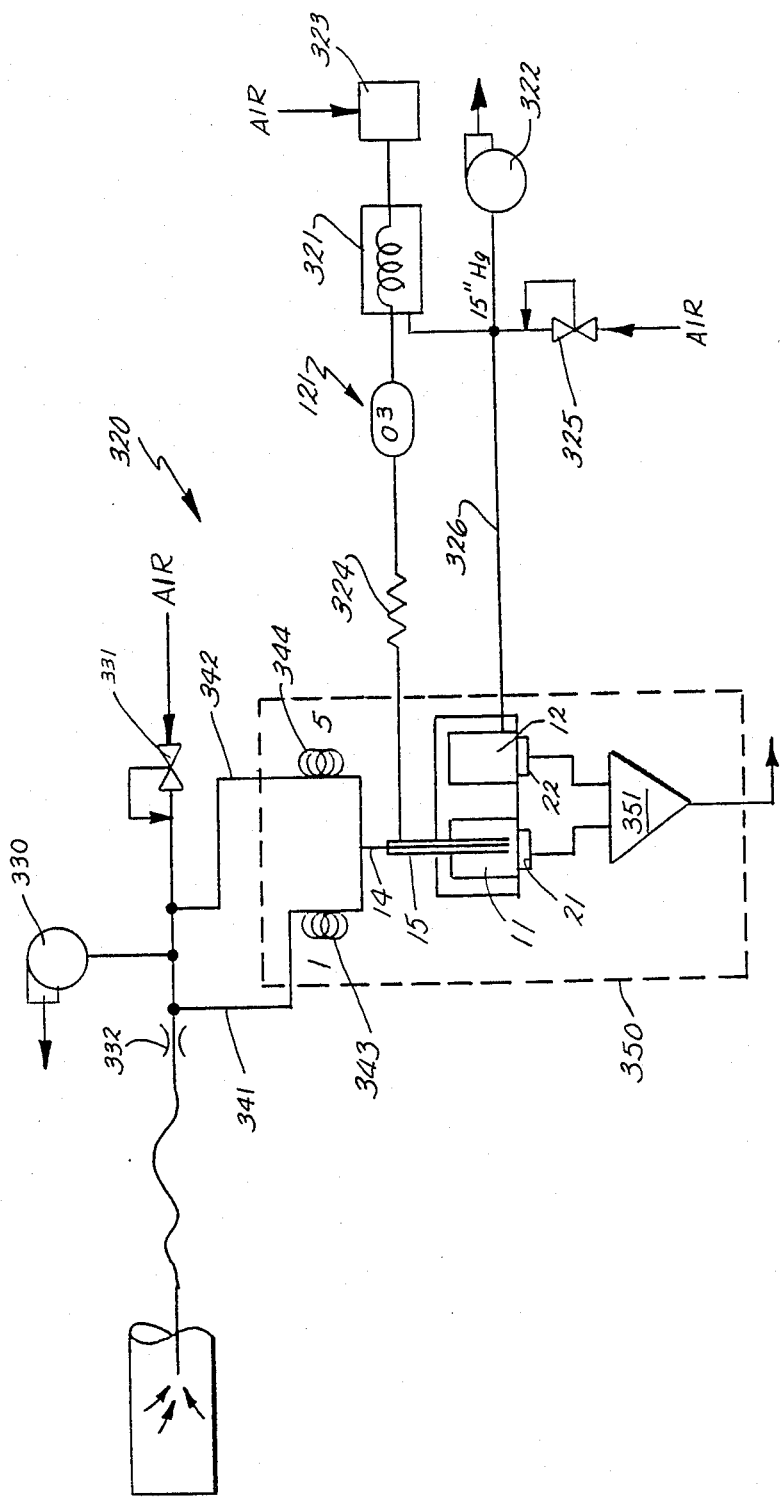
FIG. 11 is a functional diagram of another embodiment of the gas analyzer of the present invention.

With reference now to FIG. 11, a functional diagram of another embodiment of the gas analyzer of the present invention is generally illustrated at 320. The system illustrated in FIG. 11 is a simplified system which does not include a catalyst chamber 110, like that illustrated in the embodiment of FIG. 5. However, it should be understood that such a catalyst chamber may be added to the system illustrated in FIG. 11, so that measurement of total $NO_x$ is possible. The embodiment of FIG. 11 illustrates another improvement in the gas analyzer of the present invention. More particularly, it has been found that the ozonizer schematically illustrated at 121 is sensitive to relative humidity. In fact, a direct correlation between detector output in volts versus relative humidity has been observed. This can be substantially eliminated by supplying dry, pure oxygen to the ozone generator 121 or drying the atmospheric air prior to introduction to the ozone generator 121. Since the provision of a source of dry, pure oxygen is inconvenient, techniques for drying atmospheric air prior to introduction to the ozone generator 121, are the preferred solution to this problem. In one embodiment of the invention, a simple canister-like filter is provided on the input line to ozone generator 121, the canister filter being filled with a suitable desicant for substantially reducing the humidity of the incoming atmospheric air. However, in the emodiment illustrated in FIG. 11, a preferred drying technique is illustrated wherein a drying canister 321 is provided which is filled with a length of tubing which is formed from a hygroscopic ion exchange membrane which effectively removes water vapor from the gas stream flowing therethrough. Water gas molecules are transferred through the walls of the tubing and this transfer effect is facilitated by the application of approximately 15 inches of mercury vacuum by purge pump 322. A suitable ion exchange membrane extruded in tubular form is available from Perma Pure Products, Inc., 8 Executive Drive, Toms River, N.J., 08753. A suitable filter 323 is disposed at the input of drying canister 321 and a suitable floW resistance 324 is disposed on the output of the ozone generator 121. A regulator valve 325 holds the vacuum side of pump 322 to approximately 15 inches of mercury vacuum and this source of vacuum is also used to purge the sample cell 11 and reference cell 12 through line 326.

In the embodiment of FIG. 11, a simplified sample delivery system is also illustrated wherein a sample pump 330, regulated by regulator valve 331, draws an exhaust gas sample through sonic orifice 332 and a suitable supply of dilution air thrcugh regulator valve 331. Because of the effect of drier 321, it has been observed that the dilution ratio can be substantially reduced to a range of 5:1 to 2:1, of air to sample, thus substantially improving the resolution of the instrument. In this case, sample from the sonic orifice 332 and atmospheric dilution air from the regulator valve 331 are supplied to the sample tube 14 through lines 341 and 342, which include calibrated flow resistances 343 and 344 for effecting a dilution ratio of air to sample of 5:1. According to this preferred embodiment of the invention, the elements contained within the dotted lines 350, including differential preamplifier 351 are encompassed with a suitable heating coil like that illustrated in the embodiment of FIG. 9, to hold these components, and in particular, the sample and reference photodiodes 21 and 22, at a constant temperature for stabilizing the output span of the instrument.

Figure 12:
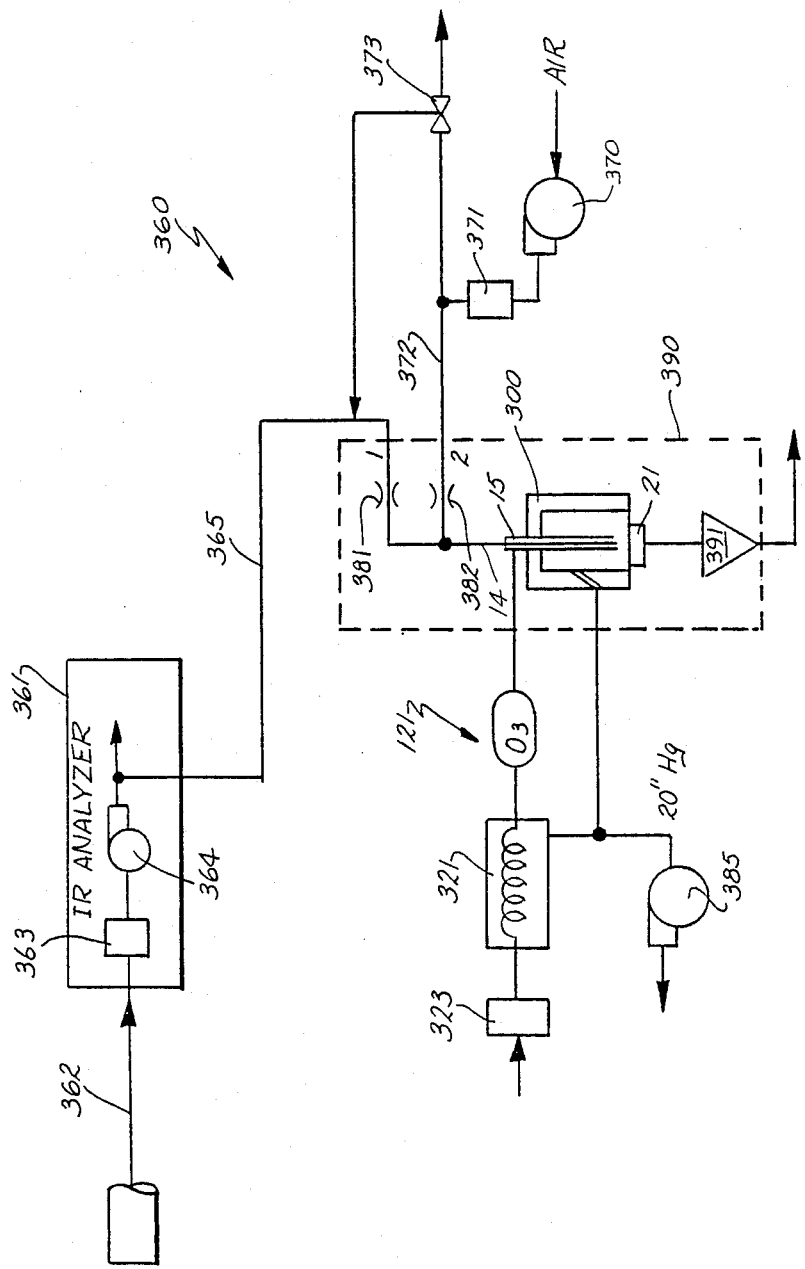
FIG. 12 is a functional diagram of another embodiment of the gas analyzer of the present invention.

With reference to FIG. 12, a functional diagram of still another embodiment of the invention is generally illustrated at 360. The gas analyzer illustrated at 360 is designed to work in conjunction with a conventional, nondispersive, infrared gas analyzer generally illustrated at 361. Such an analyzer normally draws an exhaust gas sample through line 362 and a suitable filter at 363 with a sample pump 364. The output of the sample pump 364 is then directed to the optical bench assembly of the infrared analyzer where the transmissibility of the sample with regard to certain bandwidths of infrared energy is determined to provide a measure of the concentration of certain constituents of the sample gas. In such a system, sample gas from the sample pump 364 is supplied via line 365 to the chemiluminescent nitrous oxide gas analyzer of the present invention. In this case, a positive pressure supply system is provided for supplying sample and dilution air to a single sample cell, illustrated at 300. A dilution air supply pump 370 delivers atmospheric air through filter 371 to line 372. A regulator valve 373, sensitive to the supply pressure in line 365 pressure equalizes the lines 365 and 372. A pair of sonic orifices at 381 and 382 establish a dilution ratio, which in this case is 2:1 of air to sample. The diluted sample is supplied to the sample cell 300 via concentric sample tube 14 while dry ozone is supplied to tube 15 through filter 323, drier 321 and ozone generator 121. A suitable scavenging pump 385 is used both to purge the drier 321 and scavenge sample gas from the sample chamber 300. In this preferred embodiment of the invention, the elements contained within the box 390 are all held at a constant temperature with a suitable heating coil or the like. These elements include sonic orifices 381 and 382, the sample cell 300, sample photodiode 21, as well as preamplifier 391. As in those previous embodiments which do not feature a catalyst chamber, such as the chamber 110, illustrated in the embodiment of FIG. 5, it should be understood that a suitable catalyst chamber may be provided so that the instrument is capable of providing a measure of total NO$_x$.

The above description should be considered exemplary and that of the preferred embodiment only. Modifications of the invention will occur to those who make and use the invention. It is desired to include within the scope of the present invention all such modifications of the invention that come within the proper scope of the appended claims.

The embodiments of the invention in which an exclusive property or privilege is claimed are defined as follows:

1. A gas analyzer for determining the concentration of an oxide of nitrogen in a sample gas comprising:
   a sample chamber;
   means for delivering a sample gas to said sample chamber, said sample gas containing an oxide of nitrogen;
   means for delivering ozone to said sample chamber for reading with said oxide of nitrogen and producing a chemiluminiscence;
   a sample photodiode mounted to receive light from said sample chamber and providing a sample signal representative of the concentration of said oxide of nitrogen in said sample gas; and
   means for holding said sample chamber and said sample photodiode at a constant temperature wherein a source of hot sample gas is analyzed and a sample gas line heat exchanger is provided comprising a pair of inner and outer concentric flexible lines extending from said source of hot sample gas to said analyzer, said sample gas passing through said inner line and effluent from said reference chamber passing through said outer line.

2. A gas analyzer for determining the concentration of an oxide of nitrogen in a sample gas comprising:
   a sample chamber;
   means for delivering a sample gas to said sample chamber, said sample gas containing an oxide of nitrogen;
   means for delivering ozone to said sample chamber for reading with said oxide of nitrogen and producing a chemiluminescence;
   a sample photodiode mounted to a receive light from said sample chamber and providing a sample signal representative of the concentration of said oxide of nitrogen in said sample gas; and
   means for holding said sample chamber and said sample photodiode at a constant temperture wherein a source of hot sample gas is analyzed and a sample gas line heat exchanger is provided comprising a pair of inner and outer concentric flexible lines extending from said source of hot sample gas to said analyzer, said dilution air being introduced at said aource of hot sample gas, said sample gas passing through said inner line and said dilution air passing through said outer line.

3. A gas analyzer for determining the concentration of an oxide of nitrogen in a sample gas comprising:
   a sample chamber;
   means for delivering a sample gas to said sample chamber, said sample gas containing an oxide of nitrogen;
   means for delivering ozone to said sample chamber for reading with said oxide of nitrogen and producing a chemiluminescence;
   a sample photodiode mounted to receive light from said sample chamber and providing a sample signal representative of the concentration fo said oxide of nitrogen in said sample gas; and
   a reference chamber;
   means for discharging said sample gas from said sample chamber to said reference chamber;
   a reference photodiode disposed adjacent said reference chamber for receiving light emitted from said reference chamber and providing a reference signal representative of the dark current of said sample photodiode and the background photoemissivity of said sample gas;
   means for subtracting said samlle signal and said reference signal to produce an output representative of the concentration of said oxide of nitrogen in said sample gas; and
   means for holding said sample chamber, said sample photodiode, said reference chamber and said reference photodiode at a constant temperature said means for holding comprises an electric heating means for heating said sample chamber, said sample photodiode, said reference chamber and said reference photodiode.

4. The gas analyzer of claim 3 wherein said sample photodiode and said reference photodiode are mounted on a common heat sink to provide an isothermal relationship.

5. The gas analyzer of claim 3 wherein the output of said sample photodiode and said reference photodiode are each inputted to a sample voltage follower and a reference voltage follower, respectively, said voltage followers having a high input impedance and a low leakage current.

6. The gas analyzer of claim 3 wherein said sample and reference photodiodes each comprises a low capacitance planar diffusion type photodiode.

7. The gas analyzer of claim 3 wherein said sample chamber further includes a planar light transmitting sample window.

8. The gas analyzer of claim 7 wherein said means for delivering sample gas and said means for delivering ozone to said sample chamber comprises a pair of inner and outer concentric cell tubes said cell tubes extending into said sample chamber in a direction perpendicular to said sample window and said cell tubes having open ends disposed adjacent said sample window for discharging sample gas and ozone on said sample window, whereby a chemiluminescent reaction is carried out on the surface of said sample window.

9. The gas analyzer of claim 8 wherein said open ends of said cell tubes are disposed approximately 0.020 inches from said sample window 10. The gas analyzer of claim 8 wherein said sample photodiode is provided with a planar light sensitive surface which is mounted parallel and adjacent to said sample window.

11. The gas analyzer of claim 10 further comprising a planar baffle disposed adjacent to and extending parallel to said sample window for holding the chemiluminescent reaction on said window, said cell tubes extending through said baffle.

12. The gas analyzer of claim 10 wherein said sample window is clamped between said sample chamber and said sample diode, a first opaque and heat insulating gasket being disposed between said sample chamber and said sample window and a second opaque and heat insulating gasket being disposed between said sample window and said sample diode, said second gasket establishing a small heat insulating air gap between said sample window and said sample diode.

13. The gas analyzer of claim 3 wherein said sample chamber and said reference chamber comprise a pair of cavities disposed in a common cell housing.

14. The gas analyzer of claim 13 wherein said reference chamber further includes a planar light transmitting reference window.

15. The gas analyzer of claim 14 wherein said reference photodiode is provided with a planar light sensitive surface which is mounted parallel and adjacent to said reference window.

16. The gas analyzer of claim 15 wherein said reference window is clamped between said reference chamber and said reference diode, a first opaque and heat insulating gasket being disposed between said reference chamber and said reference window; and a second opaque and heat insulating gasket being disposed between said reference window and said sample diode, said second gasket establishing a small heat insulating air gap between said reference window and said reference diode.

17. The gas analyzer of claim 15 wherein said means for discharging said sample gas from said sample chamber comprises a cross port in said cell housing, said cross port extending between said sample chamber and said reference chamber.

18. The gas analyzer of claim 17 wherein said cross port enters said reference chamber with an angular orientation that directs sample gas to said reference window, said reference chamber being provided with an exit port disposed on the back thereof behind said window.

19. A gas analyzer for determining the concentration of an oxide of nitrogen in a sample gas comprising:
 a sample chamber;
 means for delivering a sample gas to said sample chamber, said sample gas containing an oxide of nitrogen;
 means for delivering ozone to said sample chamber for reading with said oxide of nitrogen and producing a chemiluminescence;
 a sample photodiode mounted to receive light from said sample chamber and providing a sample signal representative of the concentration of said oxide of nitrogen in said sample gas; and
 means for holding said sample chamber and said sample photodiode at a constant temperature, said means for holding said sample chamber and said sample photodiode at a constant temperature comprises an electric heating means for heating the same.

20. The gas analyzer of claim 19 further comprising a sample probe adapted for placement in the exhaust gas of an internal combustion engine for determining the concentration of an oxide of nitrogen in said exhaust gas.

21. The gas analyzer of claim 20 wherein said exhaust gas is hot and a sample gas line heat exchanger is provided comprising a pair of inner and outer concentric flexible lines extending from said sample probe to said analyzer, said sample gas passing through one of said concentric lines and effluent from said reference chamber passing through the other of said concentric lines.

22. The gas analyzer of claim 21 comprising a stainless steel instrument heat exchanger for receiving sample from said line heat exchanger.

23. The gas analyzer of claim 22 further comprising a filter bowl and water trap for receiving sample from said instrument heat exchanger; and a parastoltic pump for removing condensate from said water trap and returning the same to said other of said concentric lines.

24. The gas analyzer of claim 20 further comprising a sample pump head for drawing sample gas from said sample probe into said analyzer.

25. The gas analyzer of claim 24 further comprising a sample regulator valve disposed between said sample probe and said sample pump head for introducing air to said sample pump head and establishing a predetermined sample gas pressure.

26. The gas analyzer of claim 25 further comprising a calibration valve disposed between said sample probe and said sample regulator valve, said calibration valve having a normally open port in fluid connection with said sample probe, a normally closed port in fluid connection with a source of calibration gas and said sample regulator valve and a common port in fluidconnection with said sample regulator valve for delivering gas to said sample chamber at said predetermined sample gas pressure, whereby upon actuation of said calibration valve, calibration gas is supplied to said sample chamber at said predetermined sample gas pressure.

27. The gas analyzer of claim 25 further comprising an effluent pump head for drawing sample gas from said sample chamber.

28. The gas analyzer of claim 27 further comprising an effluent regulator valve disposed between said sample chamber and said effluent pump head for introducing air to said effluent pump head and establishing a predetermined effluent gas pressure.

29. The gas analyzer of claim 5 further comprising a differential amplifier for determining the difference between the output of said sample voltage follower and said reference voltage follower, said differential amplifier having a high input impedance and a low leakage current.

30. The gas analyzer of claim 28 further comprising means for introducing dilution air into said sample gas prior to delivery of said sample gas to said sample chamber.

31. The gas analyzer of claim 30 wherein said means for introducing dilution air comprises a first flow resistance having a first predetermined value for delivering sample gas to said sample chamber from a source of sample gas at said predetermined sample gas pressure; and a second flow resistance having a second predetermined value for delivering air to said sample chamber from a source of air at said predeter:mined sample gas pressure, said first and second predetermined flow resistance values having a ratio proportional to a predetermined dilution ratio.

32. The gas analyzer of claim 30 wherein said means for introducing dilution air comprises:
 a first dilution valve having a normally open port, a normally closed port and a common port;
 a second dilution valve haviing a normally open port, a normally closed port and a common port;
 said common ports of said first and second dilution valves supplying gas to said sample chamber;
 a first flow resistance having a first predetermined value connected to said normally closed port of said first dilution valve and to a source of sample gas at said predetermined sample gas pressure;

a second flow resistance having said first predetermined value connected to said normally open port of said first dilution valve and to a source of dilution air at said predetermined sample gas pressure;

a third flow resistance having a second predetermined value connected to said normally closed port of said second dilution valve and to a source of sample gas at said predetermined sample gas pressure; and a fourth flow resistance having said second predetermined value connected to said normally open port of said second dilution valve and a source of dilution air at said predetermined sample gas pressure;

said first and second flow resistances having values proportional to a predetermined dilution ratio whereby:

a zero is established when neither of said dilution valves are actuated and only air is supplied to said sample chamber;

a low range is established when both of said dilution valves are actuated and only sample gas is supplied to said sample chamber;

a high range is established when one of said dilution valves is actuated and sample gas is supplied to said sample chamber through a flow resistance having said first predetermined value and dilution air is supplied to said sample chamber through a flow resistance having said second predetermined value.

33. The gas analyzer of claim 32 wherein said first, second, third and fourth flow resistances each comprise a viscous metering capillary tube.

34. The gas analyzer of claim 20 further comprising a diverter valve disposed between said sample probe and said sample chamber and a catalyst chamber for reducing $NO_2$ to NO, said catalyst chamber being in fluid communication with said sample chamber, said diverter valve having a normally open port connected to said sample chamber, a normally closed port connected to said catalyst chamber and a common port connected to said sample probe, whereby upon actuation of said diverter valve, sample gas is diverted through said catalyst chamber where $NO_2$ is reduced to NO and said analyzer provides an output representative of the total $NO_x$ concentration in said sample gas.

35. The gas analyzer of claim 20 further comprising means for introducing dilution air into said sample gas prior to delivery of said sample gas to said sample chamber.

36. The gas analyzer of claim 35 wherein said means for introducing dilution air further comprises means disposed on said sample probe for diluting said sample gas with air.

37. The gas analyzer of claim 36 wherein said means disposed on said sample probe for diluting comprises:

a sample sonic orifice for receiving exhaust gas;

a dilution air sonic orifice for receiving dilution air.

38. The gas analyzer of claim 37 wherein said sample probe further comprises a pressure transducer for monitoring changes in the exhaust gas pressure and thus providing a meansure of the change in an air/sample gas ratio due to changes in exhaust gas pressure and means for delivering dilution air to said dilution orifice at atmospheric pressure.

39. The gas analyzer of claim 38 further comprising a sample gas line heat exchanger comprising a pair of inner and outer concentric flexible lines extending from said sample probe to said analyzer, dilution air traveling to said sample probe through one of said concentric lines and a mixture of exhaust gas and dilution air traveling from said sample probe to said analyzer through the other of said concentric lines.

40. The gas analyzer of claim 39 further comprising a dilution pump for supplying dilution air to said line heat exchanger and said sample probe; and a dilution regulator valve disposed on the output of said dilution pump for providing dilution air at a predetermined pressure.

41. The gas analyzer of claim 38 wherein said sample orifice and said dilution orifice are provided with dimensions that are proportional to a predetermined dilution ratio.

42. The gas analyzer of claim 41 further comprising a sample pump for drawing exhaust gas and dilution air from said sample probe through said sample chamber and said reference chamber; and a sample regulator valve disposed on the input of said sample pump for establishing a predetermined sample gas pressure.

43. The gas analyzer of claim 42 further comprising a calibration valve disposed between said sample probe and said sample chamber, said calibration valve having a normally open port connected to said sample probe, a common port connected to said sample chamber and a normally closed port connected to a source of calibration gas, whereby actuation of said calibration valve supplies said calibration gas to said sample chamber.

44. The gas analyzer of calim 42 further comprising a zero valve disposed between said sample probe and said sample chamber, said zero valve having a normally open port connected to said sample probe, a common port connected to said sample chamber and a normally closed port connected to a source of air, whereby actuation of said zero valve supplies air to said sample chamber.

45. The gas analyzer of claim 41 further comprising a processor for receiving pressure signals from said pressure transducer and providing a signal representative of the actual dilution ration adjusted for the pressure of the exhaust gas.

* * * * *

UNITED STATES PATENT AND TRADEMARK OFFICE
CERTIFICATE OF CORRECTION

PATENT NO. : 4,822,564
DATED : April 18, 1989
INVENTOR(S) : Charles P. Howard

It is certified that error appears in the above-identified patent and that said Letters Patent is hereby corrected as shown below:

Column 3, line 31:
    Delete "sarple" and insert --sample--.

Column 5, line 14:
    Delete "plnr" and insert --planar--.

Column 5, line 18:
    Delete "ccndition" and insert --condition--.

Column 5, line 27:
    After "response" insert --.--.

Column 5, line 41:
    After "chemiluminescent" delete "luminescent".

Column 6, line 23:
    Delete "th" and insert --the--.

Column 7, line 8:
    After "detector" insert --.--.

Column 8, line 4:
    After "illustrated" delete "-".

Column 8, line 13:
    After "56" insert --.--.

Column 8, line 21:
    After "temperatures" delete ":" and insert --.--.

Column 8, line 40:
    After "71" insert --.--.

UNITED STATES PATENT AND TRADEMARK OFFICE
CERTIFICATE OF CORRECTION

PATENT NO. : 4,822,564

DATED : April 18, 1989

INVENTOR(S) : Charles P. Howard

It is certified that error appears in the above-identified patent and that said Letters Patent is hereby corrected as shown below:

Column 9, line 13:

After "pressure" insert --.--.

Column 9, line 27:

Delete "apprpoximately" and insert --approximately--.

Column 9, line 27:

After "minute" insert --.--.

Column 9, line 30:

Delete "intornal" and insert --internal--.

Column 10, line 32:

Delete "o" and insert --to--.

Column 11, line 11:

Delete "concentraticn" and insert --concentration--.

Column 11, line 12:

After "$NO_x$" insert --.--.

Column 11, line 43:

After "SV2" insert --.--.

Column 12, line 10:

After "probe" insert --.--.

Column 12, line 20:

After "the" delete "."

Column 12, line 30:

Delete "diuution" and insert --dilution--.

UNITED STATES PATENT AND TRADEMARK OFFICE
CERTIFICATE OF CORRECTION

PATENT NO. : 4,822,564

DATED : April 18, 1989

INVENTOR(S) : Charles P. Howard

It is certified that error appears in the above-identified patent and that said Letters Patent is hereby corrected as shown below:

Column 12, line 40:
    Delete "ccncentric" and insert --concentric--.

Column 13, line 42:
    Delete "impedanccs" and insert --impedances--.

Column 13, line 68:
    After "circuit" insert --.--.

Column 15, line 9:
    Delete "ad" and insert --and--.

Column 16, line 7:
    Delete "floW" and insert --flow--.

Column 17, line 49:
    After "to" delete "a".

Column 17, line 60:
    Delete "aource" and insert --source--.

Column 18, line 6:
    Delete "fo" and insert --of--.

Column 18, line 9:
    Delete "discharding" and insert --discharging--.

Column 18, line 17:
    Delete "samlle" and insert --sample--.

Column 18, line 39:
    Delete "comprises" and insert --comprise--.

UNITED STATES PATENT AND TRADEMARK OFFICE
CERTIFICATE OF CORRECTION

PATENT NO. : 4,822,564

DATED : April 18, 1989

INVENTOR(S) : Charles P. Howard

It is certified that error appears in the above-identified patent and that said Letters Patent is hereby corrected as shown below:

Column 18, line 56:
    After "window" insert --.--.

Column 20, line 1:
    After "claim 21" insert --further--.

Column 20, line 63:
    Delete "haviing" and insert --having--.

Column 22, line 8:
    Delete "meansure" and insert --measure--.

Column 22, line 43:
    Delete "calim" and insert --claim--.

Column 22, line 54:
    Delete "ration" and insert --ratio--.

Column 13, line 43:
    Delete "litle" and insert --little--.

Signed and Sealed this

Tenth Day of July, 1990

*Attest:*

HARRY F. MANBECK, JR.

*Attesting Officer*    *Commissioner of Patents and Trademarks*